United States Patent
Chavan et al.

(10) Patent No.: US 8,374,693 B2
(45) Date of Patent: Feb. 12, 2013

(54) SYSTEMS AND METHODS FOR TIMING-BASED COMMUNICATION BETWEEN IMPLANTABLE MEDICAL DEVICES

(75) Inventors: Abhijeet V. Chavan, Maple Grove, MN (US); Jeffrey A. Von Arx, Minneapolis, MN (US); Scott Mazar, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2142 days.

(21) Appl. No.: 11/186,245

(22) Filed: Jul. 21, 2005

(65) Prior Publication Data

US 2006/0122667 A1 Jun. 8, 2006

Related U.S. Application Data

(60) Provisional application No. 60/633,207, filed on Dec. 3, 2004.

(51) Int. Cl.
*A61N 1/32* (2006.01)

(52) U.S. Cl. ........................................................ 607/30

(58) Field of Classification Search .................. 607/16, 607/30, 32, 59, 60
See application file for complete search history.

(56) References Cited

U.S. PATENT DOCUMENTS

| | | |
|---|---|---|
| 4,791,936 A | 12/1988 | Snell et al. |
| 5,721,886 A | 2/1998 | Miller |
| 5,814,089 A | 9/1998 | Stokes et al. |
| 5,935,078 A * | 8/1999 | Feierbach ............... 600/509 |
| 6,070,103 A | 5/2000 | Ogden |
| 6,141,588 A | 10/2000 | Cox et al. |
| 6,260,152 B1 | 7/2001 | Cole et al. |
| 6,472,991 B1 | 10/2002 | Schulman et al. |
| 6,607,485 B2 | 8/2003 | Bardy |
| 6,644,322 B2 | 11/2003 | Webb |
| 6,799,280 B1 | 9/2004 | Edenfield et al. |
| 6,978,181 B1 | 12/2005 | Snell |

(Continued)

FOREIGN PATENT DOCUMENTS

| | | |
|---|---|---|
| EP | 0 928 598 | 12/1998 |
| WO | WO 03/002243 | 1/2003 |

(Continued)

OTHER PUBLICATIONS

International Search Report and Written Opinion of International Application No. PCT/US2005/43649, filed Dec. 2, 2005, both mailed Nov. 13, 2006.

*Primary Examiner* — Scott Getzow
*Assistant Examiner* — Amanda Patton
(74) *Attorney, Agent, or Firm* — Faegre Baker Daniels LLP

(57) ABSTRACT

A method carried out by an implantable medical device (IMD) for coordinating performance of one or more designated functions includes waiting in a low-power state for a predetermined event, detecting the predetermined event, and, responsive to detecting the predetermined event, searching for a wake-up command from a coordinating device implanted in the human body. The method further includes, receiving the wake-up command, and responsive to receiving the wake-up command, performing the one or more designated functions, and returning to the low-power state. A system includes a network of one or more implantable medical devices (IMDs) implanted in a human body. The system includes a satellite IMD operable to change between a plurality of power states, search for a wake-up command, and transmit an identification signal. The system may include a primary unit operable to receive the signal and coordinate a wake-up time based on the signal.

16 Claims, 5 Drawing Sheets

U.S. PATENT DOCUMENTS

| | | |
|---|---|---|
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |
| 7,013,178 B2 | 3/2006 | Reinke et al. |
| 2002/0040234 A1 | 4/2002 | Linberg |
| 2003/0114898 A1 | 6/2003 | Von Arx et al. |
| 2003/0158584 A1 | 8/2003 | Cates et al. |
| 2006/0020307 A1 | 1/2006 | Davis et al. |
| 2006/0025834 A1 | 2/2006 | Von Arx et al. |
| 2006/0031378 A1 | 2/2006 | Vallapureddy et al. |
| 2006/0038701 A1 | 2/2006 | Goetz et al. |
| 2006/0041287 A1 | 2/2006 | Dewing et al. |
| 2006/0041288 A1 | 2/2006 | Dewing et al. |
| 2006/0058627 A1 | 3/2006 | Flaherty et al. |
| 2006/0058850 A1 | 3/2006 | Kramer et al. |

FOREIGN PATENT DOCUMENTS

| | | |
|---|---|---|
| WO | WO 03/096889 | 11/2003 |

* cited by examiner

SYSTEMS AND METHODS FOR TIMING-BASED COMMUNICATION BETWEEN IMPLANTABLE MEDICAL DEVICES

CROSS-REFERENCE TO RELATED APPLICATIONS

This application claims the benefit of U.S. Provisional Application Ser. No. 60/633,207 filed on Dec. 3, 2004.

TECHNICAL FIELD

Various embodiments of the present invention generally relate to implantable medical devices and/or sensors. More particularly, embodiments of the present invention relate to systems and methods for coordinating performance of designated functions by, and interaction between, implantable medical devices (IMDs).

BACKGROUND

Description of Related Art

Medical devices are known that can be implanted within a patient's body for monitoring one or more physiologic parameters and/or to provide therapeutic functions. For example, sensors or transducers can be placed in the body for monitoring a variety of properties, such as temperature, blood pressure, strain, fluid flow, chemical properties, electrical properties, magnetic properties, and the like. In addition, medical devices can be implanted that perform one or more therapeutic functions, such as drug delivery, cardiac pacing, defibrillation, electrical stimulation, and the like. Some implantable medical devices (IMDs) on the market require patient interaction with the IMD to activate, or awaken, the IMD to perform the IMD's functions. Such a requirement for the patient can be a significant burden, particularly when multiple IMDs are involved.

Multiple IMDs can be placed at various locations throughout a person's body to perform various functions. Such disbursement can allow for a heterogeneous mix of data to be collected from various locations and can make a system more robust, since a single IMD failure typically does not effect other IMDs. As mentioned, some IMDs require the patient to activate the IMDs. IMDs can be activated through the use of some type of read relay, a magnetic device, a coil, or by inductive means. However, as the number of IMDs increases, IMD activation by the patient becomes burdensome and unrealistic.

Some IMDs include the capability for bi-directional wireless communication. Such devices can transmit data, such as measurement or status data, as well as receive data, such as commands. However, establishing a communications link with IMDs can be a particularly difficult problem, since implanted devices with internal power sources tend to be highly energy-limited. In addition, data communication between multiple IMDs has traditionally been uncoordinated and/or unmanaged, which can lead to miscommunication of therapeutic data or other adverse consequences.

Thus, a need exists for systems and methods that can coordinate and/or manage implanted medical devices.

SUMMARY

Various embodiments of the present invention relate to systems and methods for coordinating inter-device communications between implantable medical devices (IMDs). In some embodiments, a satellite IMD in a low-power state waits for a predetermined event, and upon the occurrence of the predetermined event, the IMD searches for a wake-up command from a coordinating device. Once the satellite IMD finds the wake-up command, the satellite IMD transitions to an active state and possibly performs a designated function. Information about, or gathered from, the designated function may then be communicated to the coordinating device or other satellite IMDs. Then the satellite IMD may return to the low-power state.

In some embodiments, the predetermined event is detection of a magnet near the satellite IMD. In other embodiments the predetermined event is the passing of a predetermined time. The time can be scheduled by the coordinating device. The scheduled time may be periodic. Thus, the satellite IMD may search for the wake-up command according to a schedule that may be, for example, pre-defined, periodic, or random.

Other embodiments include the exchange of time measurements between a coordinating device and the satellite devices. According to various aspects of possible embodiments, the coordinating device may determine relative time intervals and issue targeted wake-up commands based on an internal timer and the relative time intervals of the satellite devices. In other embodiments, the coordinating device may compute and/or transmit parameter corrections to the satellite device. For example, the parameter corrections may be timing corrections which can be made by adjusting an oscillator frequency. In other cases the timing corrections may be made by adjusting an oscillator divider.

Some embodiments include a plurality of satellite devices. According to various embodiments, the coordinating device may transmit parameter corrections to stagger the wake up intervals of the plurality of satellite devices.

Other embodiments generally relate to systems and methods for new IMD discovery. When an implantable medical device (IMD) is introduced into the system, the IMD may be identified and activated by the coordinating device. The new IMD may be activated by passive or active means.

According to one embodiment, once a newly introduced IMD is activated, the IMD may broadcast a request to integrate into the network which is received by the coordinating device. The coordinating device may then choose to grant or deny integration of the satellite IMD into the network. The coordinating device may then communicate with the IMD future rendezvous times, at which the IMD communicates with the coordinating device.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 1 is a diagram showing one embodiment of an arrangement of satellite IMDs communicating with a coordinator in a human body, and an external device in communication with the coordinator.

Figure 1:
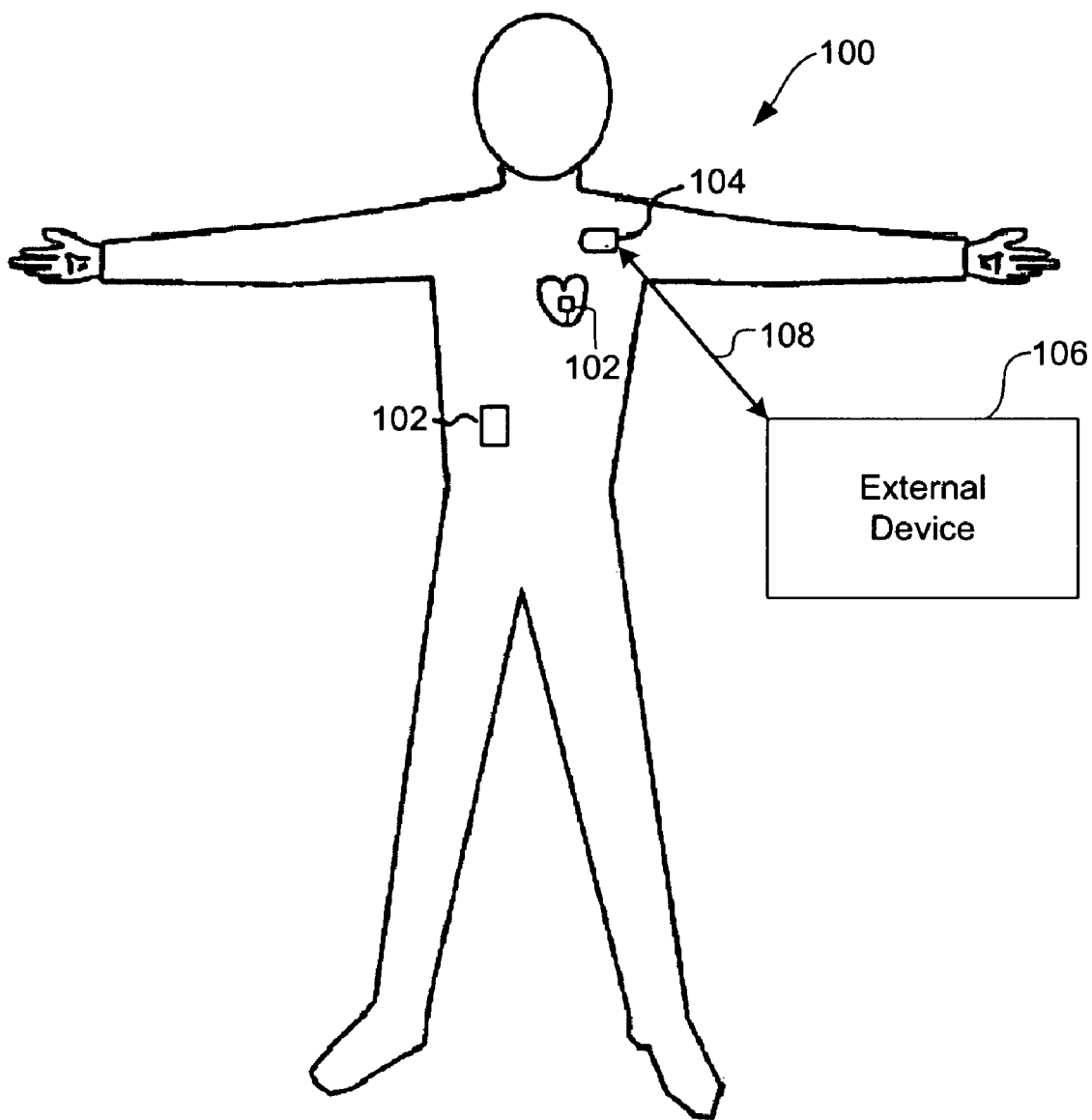

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Systems and methods are described for timing-based communications between multiple implantable medical devices (IMDs). The present disclosure describes exemplary embodiments of systems and methods using internal timers in IMDs to coordinate inter-device communications and discover new IMDs in a network/system of IMDs.

Medical devices are known that can be implanted within a patient's body for monitoring one or more physiologic parameters and/or to provide therapeutic functions. For example, sensors or transducers can be placed in the body for monitoring a variety of properties, such as temperature, blood pressure, strain, fluid flow, chemical properties, electrical properties, magnetic properties, and the like. In addition, medical devices can be implanted that perform one or more therapeutic functions, such as drug delivery, cardiac pacing, defibrillation, electrical stimulation, and the like.

It may be advantageous to have multiple satellite IMDs implanted throughout the body. The placement of multiple IMDs can enable collection of a heterogeneous mix of data from various locations and organs. In some embodiments, multiple satellite IMDs are monitored and controlled by a central coordinator. The central coordinator can have the ability to program various operating parameters of one or more of the satellite IMDs.

In some embodiments, the implantable medical devices (IMD) include the capability for bidirectional wireless communication to facilitate coordinated decentralization of IMD functions. Because establishing/maintaining a communications link between two or more IMDs can be difficult due to energy limitations of internal power sources, some embodiments employ low-power communication means. One particular embodiment uses ultrasonic waves for communicating IMD data.

Various embodiments involve using low-power (e.g., below 100 nanoamp) internal timers or oscillators to coordinate inter-device communications. In a particular embodiment, the IMDs are powered off for a majority of the time. Each IMD wakes up at scheduled times (e.g., six times/day) to perform a designated function (e.g., measurement or therapeutic function), and then transmits, via the wireless communications link, designated measurement and/or status information. In some embodiments, each IMD writes a determined time interval into the IMD's nonvolatile memory. When the time interval elapses, the IMD searches for a wake-up command.

In one embodiment, the IMDs check for a wake-up command on a frequent interval, such as each minute, hour, etc., but only for a brief period (e.g., in a range of 10 to 100 milliseconds). While checking, the devices determine if they are being commanded to fully awaken. The wake-up command can be initiated by an external or implanted coordinating device on an interval determined by external parameters. It is not necessary that the coordinating device perform a therapeutic function. In some embodiments, the coordinating device does perform a therapeutic function, e.g., cardiac rhythm management.

In cases where there is energy asymmetry between IMDs, any additional burden of coordinating link operations can be placed on the least energy-constrained device. One approach uses timers to coordinate a rendezvous time. In this approach, a timer is set according to the rendezvous time, and selected system components are powered off to conserve energy until the timer expires. At timer expiration, selected system components activate and look for environmental energy to indicate the possibility of a requested wake-up. If energy is present, then it is tested for valid "wake-up" communication link signature. If a valid wake-up signal is found, then the device changes state to activate further remaining circuit components for additional communications, computation, sensing, detection or therapy.

As discussed herein, one embodiment of the present invention relates to systems and methods for the use of internal timers to coordinate inter-device communication between IMDs. In this embodiment, the system includes an implanted primary unit, which may or may not have therapeutic value, and one or more implanted satellite devices. In one embodiment, the system can be programmable and the communications used can be wireless communications, such as acoustic communications, radio frequency communications, etc.

An example of a primary unit having therapeutic value is a cardiac rhythm management device, such as a pacemaker, defibrillator, etc. Further, the one or more satellite devices can be one or more sensors and/or therapy delivery devices, such as is disclosed in U.S. Pub. Pat. App. 2003/0158584A1 entitled "CHRONICALLY-IMPLANTED DEVICE FOR SENSING AND THERAPY" filed by Adam W. Cates et al. on Feb. 19, 2002 and published on Aug. 21, 2003, the entirety of which is incorporated by reference herein for all purposes.

In some implementations, the components of a typical satellite device could include a rechargeable battery, nonvolatile memory, an oscillator\timer, and wireless communication circuitry. In some implementations, the rechargeable batteries in/on the satellite IMD may have a capacity in the range of milliamp hours, and thus may only last for a few hours of continuous operation. Thus, the batteries can be recharged via external ultrasound equipment, for example, approximately every six months. One embodiment of a method for recharging batteries wirelessly is disclosed in U.S. Pat. No. 5,749,909, issued on May 12, 1998 and ENTITLED "TRANSCUTANEOUS ENERGY COUPLING USING PIEZOELECTRIC DEVICE," the entirety of which is incorporated by reference herein for all purposes.

Further, to help maintain battery life, the oscillator can be electrically isolated from the rest of the integrated circuit (IC) to prevent power leakage and the rest of the satellite device then can be substantially powered down to a substantially inactive state. With these power restrictions, typically the timer runs on low current, for example, about 100 nanoamps or less. In one exemplary embodiment, in order to keep the system small, a low power battery is used in conjunction with an oscillator with low power requirements, such as an RC ring oscillator. This low power oscillator may exhibit relatively low accuracy, for example, within ±10% error, and typically runs at a lower frequency, for example, around 40 kHz. For example, the timer could be a crystal oscillator. However, other embodiments could employ more accurate oscillators, such as crystal oscillators, which may have higher power requirements.

In one implementation, the satellite devices may wake up a few times per day (e.g., six) and take a measurement for a short time period (e.g., approximately 10 seconds). This measurement then can be transmitted back to the primary unit. As one skilled in the art will appreciate, there can be a number of systems and methods that can handle the "wake-up" of the satellite devices and the communication between the satellite devices and the primary unit. For example, U.S. Published Patent App. No. U.S. 2003/0114897 published on Jun. 19, 2003 by Von Arx et al., and entitled "IMPLANTABLE MEDICAL DEVICE WITH TWO OR MORE TELEMETRY SYSTEMS," and U.S. 2003/0114898 published on Jun. 19, 2003 by Von Arx et al., and entitled "TELEMETRY DUTY CYCLE MANAGEMENT SYSTEM FOR AN IMPLANTABLE MEDICAL DEVICE" disclose various "wake-up" and telemetry communication systems and methods that can be used in various implementations disclosed herein. Thus, the aforementioned patent applications are incorporated by reference herein for all purposes.

Still other implementations include methods, systems and strategies for a primary unit to communicate with the satellite devices. In such embodiments, satellite devices may be off most of the time, and may use oscillators as described above, to trigger activation of components at designated times.

In the following description, for purposes of explanation, numerous specific details are set forth in order to provide a thorough understanding of exemplary embodiments of the present invention. It will be apparent, however, to one skilled in the art that the present invention may be practiced without some of these specific details.

Terminology

Brief definitions of terms and/or phrases used throughout this application are given below. The terms "connected" or "coupled" and related terms are used in an operational sense and are not necessarily limited to a direct connection or coupling. Thus, for example, two devices may be coupled directly, or via one or more media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in one embodiment," "according to one embodiment," and the like, generally mean the particular feature, structure, or characteristic following the phrase is included in at least one embodiment of the present invention, and may be included in more than one embodiment of the present invention. Importantly, such phrases do not necessarily refer to the same embodiment.

If the specification states a component or feature "may", "can", "could", or "might" be included or have a characteristic, that particular component or feature is not required to be included or have the characteristic.

As used herein, the term "central" is not meant to indicate any particular physical position or location but rather a functional characteristic of a device. The terms "coordinating device", "coordinating IMD", "coordinator", "primary coordinator", and "primary coordinating device" are used interchangeably to refer to an implanted or external device (depending on the embodiment), which performs functions related to managing, directing, coordinating, or triggering functions and/or data to, from, within, or among implantable medical devices (IMDs).

Exemplary System

FIG. 1 illustrates a simplified human body in which a system or network 100 of implantable medical devices (IMDs) 102 performs designated functions that are coordinated by a coordinating IMD 104. Examples of designated functions include taking one, or many, physiologic measurements or providing therapy, such as pulse generation. The coordinating device 104 may or may not perform therapeutic or sensing functions. The system 100 may also include an external computing device 106, which may communicate with the coordinating device 104 via communication channel 108.

Figure 2:
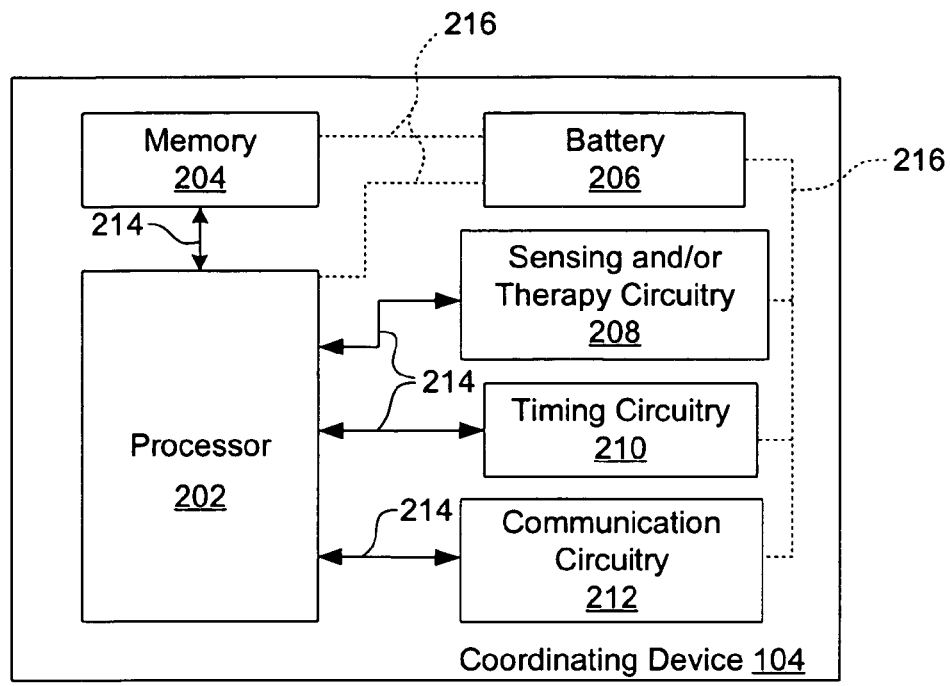
FIG. 2 is a block diagram illustrating exemplary interconnections between components and circuitry in one embodiment of the coordinator of FIG. 1.

FIG. 2 is a functional block diagram illustrating one embodiment of a coordinating IMD 104. In accordance with the illustrated embodiment, coordinating device 104 includes a processor 202, a memory 204, a battery 206, timing circuitry 210 and communication circuitry 212. In the particular embodiment illustrated, the coordinating IMD 104 also includes sensing and/or therapy circuitry 208, although in other embodiments, coordinating IMDs may not include sensing or therapy circuitry. Communication circuitry 212, timing circuitry 210, sensing and/or therapy circuitry 208 and memory 204 are in electrical communication with processor 202, as is illustrated by arrows 214. Communication circuitry 212, timing circuitry 210, sensing and/or therapy circuitry 208, memory 204 and processor 202 are electrically coupled with battery 206, as is illustrated by dotted lines 216.

As one skilled in the art will appreciate, processors and memory devices are well known in the art, and the specific type and/or style of processor or memory device that can be used in coordinating IMD 104 is not limited. Accordingly, processor 202 can be any suitable processing device, or devices, currently known or later developed, and memory 204 can be any suitable memory device, or devices, currently known or later developed.

The steps performed by the IMDs in various embodiments may be embodied in machine-executable instructions. For example, the instructions may be used to cause a general-purpose or special-purpose processor within the IMD that is programmed with the instructions to perform the steps. Thus, for example, memory 204 may include code and/or data that can be read and/or executed by processor 202. Alternatively, the various steps may be performed by specific hardware components that contain hardwired logic for performing the steps, or by any combination of programmed computer components and hardware components. According to various embodiments, an IMD (e.g., IMD 102, 104) may contain firmware which is capable of being updated. Parts of the firmware may include instructions which may be used to program a computer (or other electronic devices) to perform a process according to embodiments of the present invention.

Communication circuitry 212 is circuitry that allows the coordinating IMD 104 to communicate with other devices, such as external computing device 106 or a satellite IMD 102. As discussed above, the coordinating IMD 104 can communicate with other devices via a wireless connection. As one skilled in the art will appreciate, various types of wireless communication circuitry are well known in the art, and the specific type and/or style of wireless communication that can be used is not limited. For example, ultrasonic waves, acoustic communications, radio frequency communications, and the like may be used by the communication circuitry. In some embodiments, an acoustic carrier may be modulated with techniques such as amplitude shift key (ASK), on-off shift keying (OOSK), and the like.

The timing circuitry 210 performs functions related to scheduling, prompting, activating, etc. various activities to be performed by the IMD 102. In the coordinating IMD 104, at least according to one embodiment, the timing circuitry may be an internal timer or oscillator. According to various other embodiments, timing may be performed by specific hardware components that contain hardwired logic for performing the steps, or by any combination of programmed computer components and custom hardware components. In some embodiments, the timing circuitry 210 on the coordinating IMD 104 has a higher level of accuracy than that of the satellite devices 102. The time generated by the timing circuitry 210 may then be utilized by other components in the IMD 104, e.g. the processor 202, in one or more calculations. For example, in one embodiment, the timing circuitry 210 is utilized to determine the appropriate time at which one or more satellite IMD 102 should wake in order to perform a designated function. In other embodiments, the timing circuitry may be used to generate a reference against which the timing drift of one or more satellite devices 102 may be measured.

The sensing and/or therapy circuitry 208 is not limited to any particular type of physiologic measurement or therapy. Examples of possible physiologic measurements include blood pressure, temperature, blood or fluid flow, strain, electrical, chemical, or magnetic properties within the body. The therapeutic functions are also not limited to any particular type and can include, for example, providing heart pacing therapy, cardiac defibrillation therapy, cardiac resynchronization therapy, drug delivery therapy, or any other therapy capable of being administered with an IMD currently known or later developed.

Figure 3:
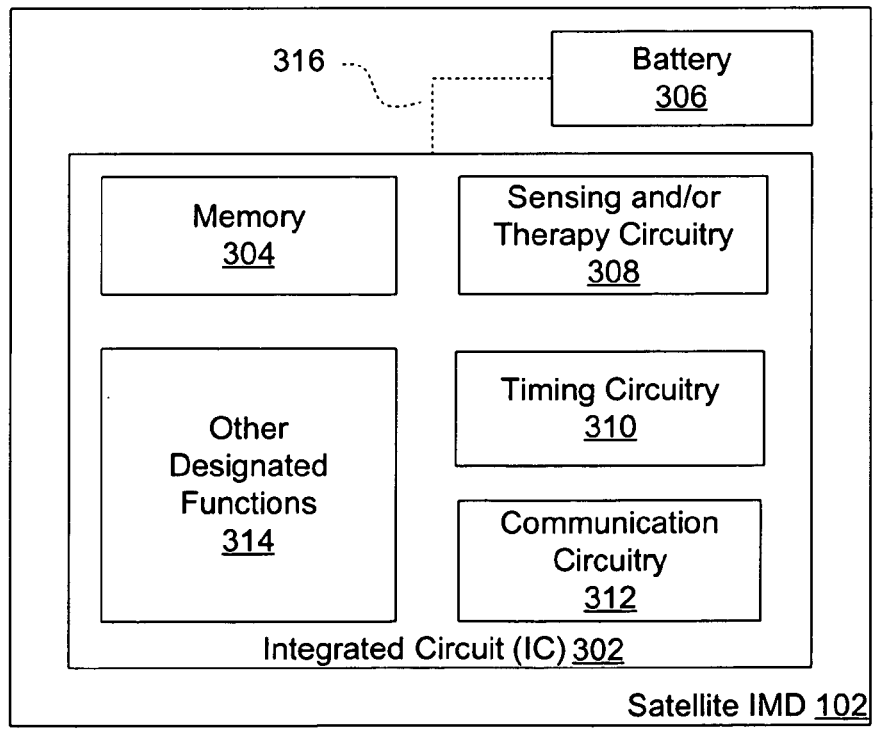
FIG. 3 is a block diagram illustrating exemplary interconnections between components and circuitry in one embodiment of a satellite device of FIG. 1.

FIG. 3 is a functional block diagram illustrating one embodiment of a satellite IMD 102. In accordance with the illustrated embodiment, IMD 102 includes an integrated circuit (IC) 302 which contains a memory 304, sensing and/or therapy circuitry 308, timing circuitry 310 and communication circuitry 312. In addition to the IC 302, the satellite IMD 102 has a rechargeable battery 306. Communication circuitry 312, timing circuitry 310, sensing and/or therapy circuitry 308 and memory 304 are in electrical communication within the IC 302. Communication circuitry 312, timing circuitry 310, sensing and/or therapy circuitry 308, memory 304 and integrated circuit 302 within the IC are electrically coupled with battery 306, as is illustrated by lines 316.

In some embodiments, IC 302 is a specialized or general-purpose component that facilitates performance of designated functions 314. The IC 302 can be a digital signal processor, a microprocessor, an application-specific IC (ASIC), for example. The IC 302 may execute software resident in memory 304. In some embodiments, memory includes a data table having timing data that the IC 302 uses to program the timing circuit. For example, the data table may have value(s) representing timing interval(s) designating when the IMD 102 should wake-up or become activated.

The steps performed by satellite IMDs 102 in various embodiments may be embodied in machine-executable instructions. For example, the instructions may be used to cause a general-purpose or special-purpose processor or an ASIC within the IMD 102 that is programmed with the instructions to perform the steps. Alternatively, the various steps may be performed by specific hardware components that contain hardwired logic for performing the steps, or by any combination of programmed computer components and custom hardware components. According to various embodiments, an IMD 102 may contain firmware which is capable of being updated. Parts of the firmware may include instructions which may be used to program a computer (or other electronic devices) to perform a process according to embodiments of the present invention.

Communication circuitry 312 is circuitry that allows the satellite IMD 102 to communicate with other devices, such as external computing device 106 or coordinating IMD 104. As discussed above, the satellite IMD 102 can communicate with other devices via a wireless connection. As with the coordinating device 104 the specific type and/or style of wireless communication that can be used is not limited. For example, ultrasonic waves, acoustic communications, radio frequency communications, and the like may be used by the communication circuitry.

The sensing and/or therapy circuitry 308 performs functions related to measurement of physiologic parameters and/or therapy, and are not limited to any particular type of physiologic measurement or therapy. Examples of possible physiologic measurements include blood pressure, temperature, blood or fluid flow, strain, electrical, chemical, or magnetic properties within the body. Examples of therapeutic functions include providing heart pacing therapy, cardiac defibrillation therapy, cardiac resynchronization therapy, drug delivery therapy, or any other therapy capable of being administered with an IMD currently known or later developed.

The timing circuitry 310 performs functions related to scheduling, prompting, activating, etc. various activities to be performed by the IMD 102. In one particular embodiment the timing circuitry 310 employs low-power (e.g., below 100 nanoamp), internal timers or oscillators to coordinate inter-device communications. In a particular embodiment, selected components in the IMDs 102 are powered off for a majority of the time. Timing circuitry 310 can cause selected components of the IMD 102 to wake up at a scheduled time. The timing circuitry 310 can then generate a signal that prompts further activation of IMD 102 components. For example, the sensing and/or therapy circuitry 308 may be activated to perform designated therapy or sensing functions. According to various embodiments, timing may be performed by specific hardware components that contain hardwired logic for performing the steps, or by any combination of programmed computer components and custom hardware components.

Exemplary Algorithms

Exemplary embodiments of algorithms are shown and discussed below for coordinating functions and data flow among multiple IMDs in a network of IMDs. Such coordination involves, for example, enabling communication between the IMDs and a coordinating device. In accordance with embodiments described herein, effective communication is facilitated by timing devices internal to the IMDs and the coordinating devices. These timing devices generally enable selection of times when the IMDs and coordinating device communicate. In general, each internal timing device operates based on a timing reference.

In accordance with various embodiments, components in the IMDs that provide a timing reference are configured to use relatively small amounts of current in order to conserve energy. Examples of such timing reference components are oscillators, such as RC relaxation, LC tuned circuit and crystal stabilized. Within such devices, timing fluctuations may result from the stochastic nature of the flow of low currents. Further, the absolute timing precision of a low current oscillator may be uncertain due to uncertainty and difficulty of fabrication of exact component values.

With these factors in mind, embodiments can manage timing uncertainty in a multiple-device network by burdening the least power-constrained component. In an exemplary embodiment, a wake-up signal is issued by the coordinating device. The wake-up signal begins to be broadcast prior to the time when the first highly energy-constrained device (e.g., a satellite IMD) will likely wake-up. The wake-up broadcast lasts until it is estimated that all device time uncertainties have been covered and full system wakeup occurs. To illustrate how such an approach may be implemented, FIG. 4 illustrates an algorithm having exemplary operations for waking up an IMD and triggering the IMD to perform designated functions.

Figure 4:
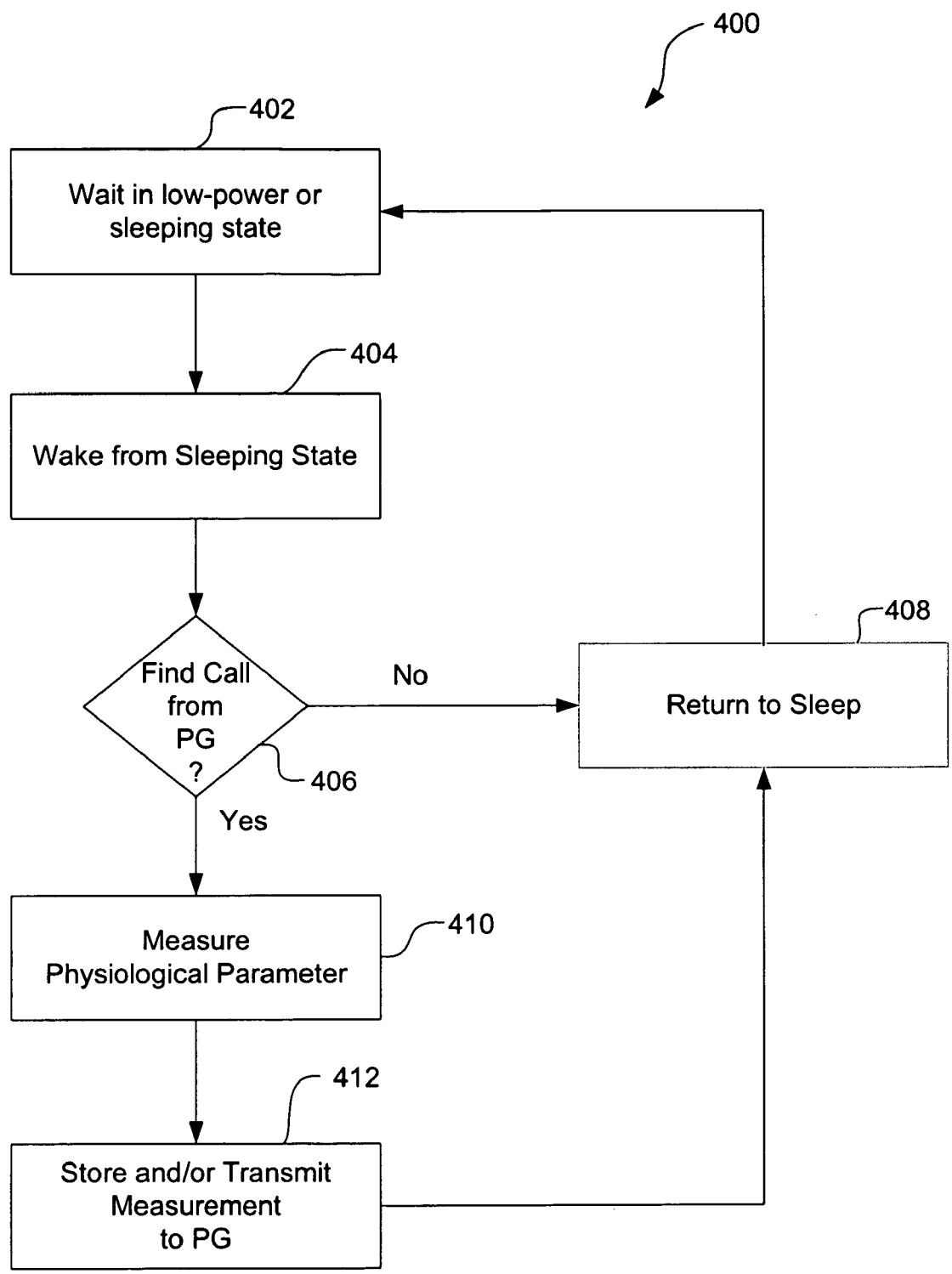
FIGS. 4-5 are flow charts illustrating various embodiments of methods to coordinate inter-device communications and managing and/or adapting to time interval uncertainty.

FIG. 4 is a flow chart illustrating an exemplary algorithm 400 for coordinating performance of designated functions by one or more satellite IMDs. The algorithm 400 is typically carried out by a satellite IMD. In this particular embodiment, it is assumed that the satellite IMD includes a sensor and performs designated measurement functions. Performance of the measurement functions is coordinated by a coordinating IMD. In the illustrated embodiment, coordinating measurement involves triggering measurement at scheduled time(s) and managing inter-device communications intervals. In this particular embodiment, it is assumed that the coordinating IMD is a pulse generator (PG) for illustrative purposes. In this embodiment, the satellite IMD can use internal timers to facilitate coordination of data communications and performance of designated functions.

In order to conserve energy, the satellite IMD will generally be in a low-power, or sleeping, state with only the timer running. As such, initially, the IMD performs a waiting operation 402. The waiting operation 402 waits for an event to occur and then leaves the sleeping state. In this embodiment, the event is a scheduled time. For example, the waiting operation 402 may periodically leave the sleeping state (e.g., once per minute). When the waiting operation 402 detects the scheduled time, an activating operation 404 activates a search for a predetermined signal from the coordinating IMD.

In one embodiment of the activating operation 404, the IMD activates a minimal amount of circuitry in order to search for a valid "wake-up" signal. In this sense, the activating operation 404 puts the sensor in an intermediary state between a fully activated state and the sleeping state. The sensor then analyzes received signals to determine if the signals have characteristics of a predetermined wake-up signal.

In some embodiments, the wake-up signal includes information that identifies the signal as the wake-up signal from the coordinating IMD. In a particular embodiment, the wake-up signal includes a communication link signature that is inserted into the signal by the coordinating IMD. The communication link signature is a predetermined pattern of data that identifies the coordinating IMD with a relatively high degree of likelihood. While the communication link signature does not need to be unique among all coordinating IMDs, the communication link signature is typically selected such that the probability is low that any two coordinating IMDs that get close to each other will not share the same signature.

If the sensor does not find a valid wake-up signal, then the sensor returns to sleep in returning operation 408. Returning operation 408 powers the sensor back down to the low-power state. If, however, the sensor does find a valid wake-up signal, then the sensor takes the physiologic measurement(s) in a measuring operation 410. In one embodiment, measuring operation 410 changes state of the sensor by further activating remaining sensor circuit components, such as, but not limited to, sensing circuitry, communications circuitry, and computation circuitry.

As discussed above, the sensor is not limited to any particular physiologic measurement. Examples of possible physiologic measurements include blood pressure, temperature, blood or fluid flow, strain, electrical, chemical, or magnetic properties within the body. Once the sensor has taken the measurement(s), the results may be stored in the satellite IMD, and/or transmitted to the central coordinator IMD in storing/transmitting operation 412. Following storing/transmitting operation 412, the sensor returns to sleep in returning operation 408. The algorithm 400 typically is repeated, for example, on a periodic basis.

The previously discussed wake-up scheme, which attempts to take into account variability in IMD time reference, may not be optimally energy-efficient for the coordinating device, because an extended wake-up broadcast may be necessary to cover all remote device time uncertainties. Thus, in another, perhaps more energy-efficient embodiment, once the system is fully awake, time data can be exchanged between the coordinating device and other IMDs to determine relative time intervals or references.

In this embodiment, exchanged time information remains resident in the coordinating device. When the coordinating device wakes, the coordinating device will use its internal time reference, and data about other devices' relative time references to issue targeted wake-up commands and bring the network on-line. Use of shorter wake-up commands may conserve signaling energy used by the coordinating device.

Another embodiment of a method of waking time-coordinated IMDs is similar to the previous method except that once the relative time intervals of satellite devices is known by the coordinating device, intervals are communicated back to the satellite devices and used for time-base correction. Time-base correction may be implemented by adjusting the oscillator frequency or by adjusting an oscillator divider if the oscillator runs at approximately a multiple of the rendezvous intervals. The correction factor is stored in each satellite device and the coordinator only issues a single wake-up command with a time duration that is dependent on known oscillator uncertainties.

In yet another embodiment, the satellite device counts the oscillator cycles until a desired number of counts, which may be stored in a register, is reached. Once the count stored in the register has been reached, the satellite device will wake-up. In this embodiment, the correction factor that is sent by the coordinating device is a revised count, which is adjusted to compensate for the timer drift in the satellite device.

Time Reference Drift

Factors exist that may affect the long and short-term certainty of a time reference. Exemplary factors are component aging, ambient temperature, oscillator operating voltage and so on. Some embodiments for correcting long-term drift include periodic recalibration using the methods described above. Short-term drift due to factors like electron-induced oscillator noise, particularly at low currents, can cause uncorrelated stochastic variations between references in each device.

In some embodiments, short-term variations or drift can be compensated by progressively increasing the wake-up command duration based on time elapsed since the last coordinated communication. In particular, satellite IMDs can reset their time clocks either on command by the coordinating device or by keying on a received data feature such as the ending of the wake-up command, thereby resetting inter-device time uncertainty periodically.

In some embodiments, time reference uncertainty and the coordinator's budgeted energy for communications are determinants of the maximum interval between communications for timing resynchronization. The energy constraints on the satellite device along with physiological needs may be used for determining the minimum time between satellite device wake-ups in some embodiments. To illustrate implementations that take advantage of the foregoing concepts, FIG. 5 depicts an algorithm that can be used to determine and adjust for variations in time references among IMDs.

Figure 5:
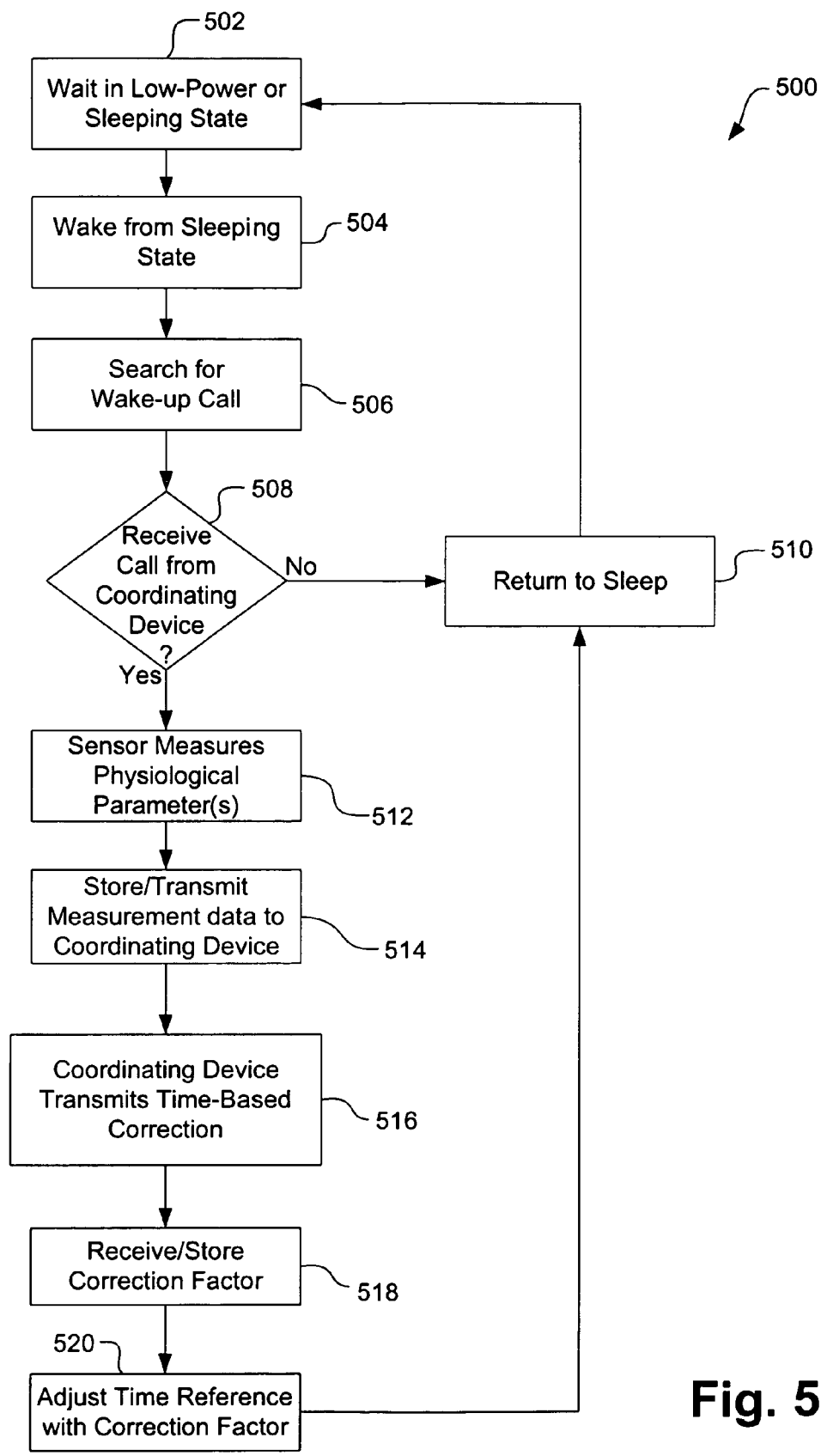

FIG. 5 is a flow chart illustrating an algorithm 500 for coordinating satellite IMD measurement schedule, inter-device communications intervals, and corrections of timing errors. In this embodiment, the IMDs use internal timers for coordination. Similar to the algorithm 400 of FIG. 4, the satellite device waits in a low-power or sleeping state in waiting operation 502 in order to conserve energy. In waiting operation 502 only the timer is running. When a predetermined event occurs, such as a scheduled time, waking operation 504 wakes the sensor into a more activated, but not fully activated state. The waking operation 504 activates enough sensor circuitry sufficient to search for a predetermined wake-up call from the coordinating IMD.

A searching operation 506 then searches for the predetermined wake-up signal. As discussed above, the wake-up signal has characteristics that are searched for. The wake-up signal can include a communication link signature that identifies the signal as being from the coordinating device. Query operation 508 analyzes received signal(s) to determine if they are the wake-up call.

If a valid wake-up signal is not received, then query operation 508 branches to returning operation 510. Returning operation 510 puts the sensor back into the low-power, sleeping state. If, however, the sensor does find a valid wake-up signal, query operation 508 branches to measuring operation 512. Some embodiments of the measuring further activate the sensor to perform designated functions, such as, but not limited to, sensing physiologic parameter(s), and communicating, storing, and/or analyzing data. After activation, the measuring operation 512 measures one or more designated physiologic parameter(s).

After measuring operation 512, a storing/transmitting operation 514 stores measurement data or transmits measurement data to the coordinating device. In response, the coordinator will determine a time-base correction that can be used to account for time reference drift between the satellite sensor and the coordinating device. The coordinator then transmits the determined time-base correction to the sensor in transmitting operation 516. In a receiving operation 518, the sensor receives, and may store, the time-base correction.

An adjusting operation 520 uses the time-base correction to adjust the time reference of the sensor. In one embodiment, the adjusting operation 520 adjusts the oscillator frequency. In another embodiment, the adjusting operation 520 adjusts the oscillator divider if the oscillator runs at approximately a multiple of the rendezvous intervals. In yet another embodiment, the adjusting operation 520 adjusts the count value in a register in the satellite device. In any event, once the sensor adjusts the time reference using the correction factor, the sensor returns to sleep in returning operation 510.

Exemplary New Device Discovery and Timing Intervals for New Devices

Some embodiments of IMD networks include mechanisms for introducing a new device into the system/network. In one embodiment, an external device is used to wake the coordinator and satellite IMD and allow the devices to communicate to coordinate future rendezvous times. In this case, both the coordinator and new satellite device check for environmental signal activity on a periodic basis, and an external device (e.g., external device 106, FIG. 1) generates a super-system wake-up command that is recognized by the IMDs and coordinating device in the network. After being wakened by the external device, control is handed off to the coordinator.

In another embodiment, the satellite IMD is activated by a passive device (such as a magnet) or active external device, and begins broadcasting a signal including request to integrate into the network. The coordinator detects and acts on the request at the next system wake-up interval. Once activated, the remote device can periodically listen to see if it has been acknowledged. Further, in some embodiments, the coordinator can check for the environmental signal periodically.

In yet another embodiment, the coordinator can send an extended "all call" broadcast periodically to determine if new devices have been added to the system. This architecture may incur a time delay before recognizing a new device and therefore limit the in-network testability of the new remote device.

In still another embodiment, the satellite device is introduced to the network and then the coordinator device is commanded to search for new network devices through either the network communications channel or an alternate communications channel. Since the coordinating device typically has the bigger battery, the coordinating device is typically activated first, and "listens" for a signal from a satellite device for a predetermined period (e.g., one minute). During this period, the satellite device may be activated, for example, through an external passive device. Once recognized by the coordinator, the satellite device is then integrated into the network.

Figure 6:
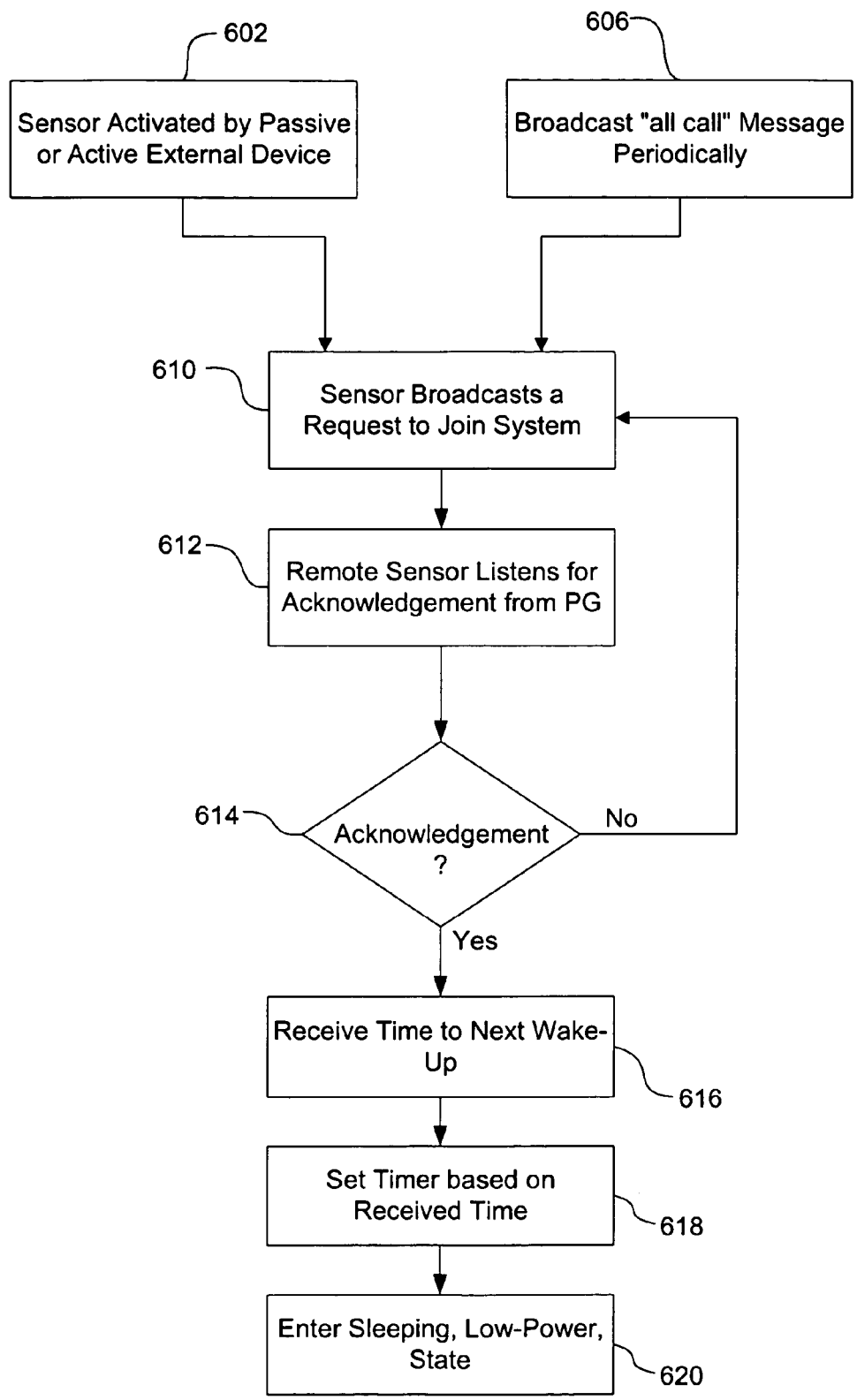
FIG. 6 is a flow chart illustrating various embodiments of methods for recognizing a new IMD in a network/system of IMDs.

FIG. 6 is a flow chart illustrating an exemplary algorithm 600 including two alternative embodiments of new device discovery, activation and integration into a network of implantable medical devices (IMDs). In these alternative embodiments, for illustrative purposes, the IMD(s) to be added are sensors. In other embodiments, the IMDs can provide therapy. In addition, the alternative embodiments are not mutually exclusive; thus, they can be used together, depending on the particular design.

In one of the alternative embodiments, an activating operation 602 activates a new sensor. In this embodiment, the sensor may be activated by a passive or active external device. An example of passive activation is the use of a magnet. In another alternative embodiment, a broadcasting operation 606 broadcasts a predetermined message to determine if new devices have been added to the network. In one embodiment of the broadcasting operation 606, the coordinator periodically sends an "all call" broadcast in search of new network devices.

The remaining operations of the two embodiments are similar. In a transmitting operation 610, a new sensor transmits a request to join the network. Transmitting can be in response to being activated by activating operation 602 or in response to receipt of an "all call" broadcasting message. In a listening operation 612, the new sensor listens for acknowledgement from the coordinator.

In one embodiment of the listening operation 612, the new sensor monitors for a predetermined signal from the coordinator that indicates the sensor can join the network (i.e., acknowledged). When a signal is received, a query operation 614 analyzes the signal to determine if the new sensor is acknowledged. If the sensor is not acknowledged, query operation 614 branches back to the broadcasting operation 610. If the sensor is acknowledged, querying operation 614 branches to a receiving operation 616. In receiving operation 616, the sensor receives a signal from the coordinator that indicates a time to wake-up next.

In a setting operation 618, the sensor sets an internal timer according to the time received in the receiving operation 616. Setting operation 618 may set a count value in a register and start a counter counting down from the count value. In an entering operation 620, the sensor enters a low-power, or sleeping state. In one embodiment of the entering operation 620, power is removed from all sensor circuitry except for the timer circuitry. Thus, while in the low-power state, the timer continues to monitor the time, and when the wake-up time is reached, the timer will trigger the sensor to reactivate.

Timing for Multiple Satellite IMDs

As described above, the coordinator is able to program the future rendezvous times of the satellite devices. This ability will allow the coordinator to stagger the waking times of multiple satellite devices in order to stay within communication parameter limitations of the coordinator.

Conclusion

In conclusion, embodiments of systems and methods use internal timers to coordinate inter-device communications between IMDs and a coordinator. Some embodiments include means for managing and handling time interval uncertainty in IMDs. Some embodiments provide for detection and introduction of new IMDs in a network of IMDs.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method carried out by an implantable medical device (IMD) for coordinating performance of one or more designated functions, the IMD being implantable in a human body, the method comprising:
   waiting in a low-power state for a predetermined time event, wherein only timing circuitry within the IMD is activated in the low-power state;
   detecting the predetermined time event;
   responsive to detecting the predetermined time event, activating communication circuitry within the IMD and searching for a wake-up command from a coordinating device implanted in the human body;
   receiving the wake-up command;
   responsive to receiving the wake-up command, performing the one or more designated functions; and
   returning to the low-power state.

2. The method as recited in claim 1, further comprising transmitting a signal to the coordinating device, the signal identifying the IMD.

3. The method as recited in claim 1, wherein the predetermined time event is passage of a scheduled time.

4. The method as recited in claim 3, wherein the scheduled time is retrieved from a look up table.

5. The method as recited in claim 3, wherein the scheduled time is set in a programmable timer.

6. The method as recited in claim 3 further comprising:
   receiving time interval data from the coordinating device, the time interval data designating the scheduled time; and
   setting a timer in the IMD based at least in part on the time interval data.

7. The method as recited in claim 3 further comprising:
   receiving time correction data from the coordinating device; and
   setting a timer based on the time correction data.

8. The method as recited in claim 7, wherein setting the timer comprises adjusting an oscillator frequency, adjusting an oscillator divider, or setting a count value in a register.

9. The method as recited in claim 1, wherein receiving the wake-up command comprises receiving a carrier signal modulated with on-off shift keying.

10. The method as recited in claim 1, wherein receiving the wake-up command comprises receiving an ultrasonic signal.

11. The method as recited in claim 1, wherein at least one of the one or more designated functions includes measuring a physiologic parameter.

12. The method as recited in claim 1, wherein at least one of the one or more designated functions includes administering a therapy.

13. The method as recited in claim 1, wherein the coordinating device is operable to perform a therapeutic function.

14. A method carried out by an implantable medical device (IMD) for coordinating performance of one or more designated functions, the IMD being implantable in a human body, the method comprising:
   scheduling a timing event within timing circuitry of the IMD, the timing circuitry configured to selectively activate one or more components of the IMD between a low-power state and an active state;
   waiting in a low-power state for the scheduled timing event to elapse, wherein only the timing circuitry is activated in the low-power state;
   responsive to the elapsed timing event, activating communication circuitry within the IMD and searching for a wake-up command from a coordinating device implanted in the human body;
   receiving the wake-up command;
   responsive to receiving the wake-up command, performing the one or more designated functions; and
   returning to the low-power state.

15. A method carried out by an implantable medical device (IMD) for coordinating performance of one or more designated functions, the IMD being implantable in a human body, the method comprising:
   scheduling a timing event within timing circuitry of the IMD, the timing circuitry configured to selectively activate one or more components of the IMD between a low-power state and an active state;
   waiting in the low-power state for the scheduled timing event to elapse, wherein only the timing circuitry is activated in the low-power state;
   responsive to the elapsed timing event, activating communication circuitry within the IMD and searching for a wake-up command from a coordinating device implanted in the human body;
   receiving the wake-up command;
   responsive to receiving the wake-up command, activating one or more sensors within the IMD and sensing pressure or flow within the body; and
   returning to the low-power state.

16. The method of claim 15, wherein activating communication circuitry within the IMD and searching for a wake-up command from a coordinating device implanted in the human body includes activating the IMD in an intermediary power state between the low-power state and a fully active state.

* * * * *